United States Patent

Mally

Patent Number: 5,327,912
Date of Patent: Jul. 12, 1994

[54] X-RAY POSER

[76] Inventor: Mitchell R. Mally, 4315 Washington St., Davenport, Iowa 52806

[21] Appl. No.: 919,307
[22] Filed: Jul. 24, 1992
[51] Int. Cl.⁵ .............................................. A61F 5/04
[52] U.S. Cl. ..................................... 128/878; 378/180
[58] Field of Search ............... 378/180, 175, 208, 177, 378/179; 128/877, 878, 879, 881, 882, 845; 5/601, 623, 647, 646

[56] References Cited

U.S. PATENT DOCUMENTS

| | | |
|---|---|---|
| 2,146,913 | 6/1938 | Piotrowski ........................ 378/175 |
| 2,989,634 | 6/1961 | Ould et al. . |
| 3,302,021 | 1/1967 | Hardy ............................... 378/180 |
| 3,521,876 | 7/1970 | Smith ................................ 378/180 |
| 3,639,764 | 2/1972 | Olson ............................... 378/175 |
| 3,715,587 | 2/1973 | Burkhalter et al. . |
| 3,873,841 | 3/1975 | Cabansang ......................... 5/601 |
| 4,045,678 | 8/1977 | Rickard . |
| 4,320,749 | 3/1982 | Highley ............................. 378/180 |
| 4,323,080 | 4/1982 | Melhart . |
| 4,504,050 | 3/1985 | Osborne . |
| 4,719,646 | 1/1988 | Saunders ........................... 378/179 |
| 4,827,496 | 5/1989 | Cheney ............................. 378/180 |

Primary Examiner—Robert A. Hafer
Assistant Examiner—David Kenealy
Attorney, Agent, or Firm—Willian Brinks Hofer Gilson & Lione

[57] ABSTRACT

An appliance in which a patient's forearm and hand can be secured by straps at a prescribed angle that will enable X-ray pictures to be made at a specific angular relationship each time a X-ray is made so that the physician can evaluate the patients condition and changes in the patient's condition over a treatment period.

13 Claims, 2 Drawing Sheets

X-RAY POSER

FIELD OF THE INVENTION

The present invention relates generally to an assembly for supporting a human body joint in a fixed prescribed position to facilitate radiographic examination of the human body joint.

BACKGROUND OF THE INVENTION

When taking an X-ray of any area of the body it is important that the body part be properly posed such that the condition under examination will be displayed optimally to reveal the information needed to be analyzed or treat the patient. Proper posing becomes even more critical when a body joint is being examined. In such a situation the relative position of multiple parts of the body is critical. Practices that are currently used are, for example, to have the patient hold the hand of the wrist that is to be X-rayed with his or her other hand or to wrap a towel around the hand of the wrist that is to be X-rayed and pull on the towel with the other hand to bend the wrist at a desired angle. However any technique, in which the physician or an X-ray technician instructs the patients in how the joint should be properly posed, and relies on the patient to maintain such a proper pose, will result in numerous errors requiring repeat x-rays. When using such techniques there is no assurance that the patient will maintain his or her arm joint as it was instructed to be posed. The physician or X-ray technician would become overexposed to X-ray if he or she were to remain with the patient to assure that the proper pose is retained. Furthermore the angle of a joint that is to be X-rayed can, in some situations, be so critical that an error of several degrees in the angulation may render the results useless or less than optimum. If repeat X-rays are required, the patient is exposed to additional doses of radiation, with no assurance that the correct angulation will be attained in the subsequent X-ray. This problem becomes even more critical in medical situations in which it is necessary to compare a series of X-rays to chart the progress of the treatment and healing. A patient in this situation will be exposed to considerable amounts of X-rays during the course of the treatment and the duplication of failed attempts could easily over expose the patient to X-rays. Furthermore in the process of comparing one X-ray to another in a series it is essential that all X-rays be taken at the identical angle. In these situations a device for posing a joint at a precise angle that is known to optimize the usefulness of the X-ray is required.

Such a situation exist in the treatment of wrist injuries caused from repetitive motion. The disorders go by many names including carpal tunnel syndrome, tendinitis or general terms such as repetitive strain injury. This painful disorder of the wrist and hand is induced by compression on the median nerve by bones and other structures that have become displaced within the carpal tunnel. The disorder can be successfully treated by relocating the bones and other structures of the carpal tunnel to their proper position, without recourse to surgery provided the displacement within the carpal tunnel is accurately diagnosed and then properly treated. A prerequisite to such treatment is the accurate diagnosis and understanding of the displaced condition that exist in the carpal tunnel. An X-ray of the area, taken at the proper angle is an essential part of this diagnosis. It has been found that after treatments there can be a partial retroceding of the prior condition, and a series of treatments are required to attain a permanent correction. For this reason it is important that the progress from one treatment to the next be accurately measured and documented. Reliable comparisons can only be made if the X-rays being compared were taken at the same precise angle. In the treatment of carpal tunnel syndrome it has been found through extensive experimental work that the optimum angle to X-ray the carpal tunnel is 70°. At a 70° angle the bony and other structures in the carpal tunnel are seen at maximum visibility relative to each other. It has been found that this optimum angle, of 70° is valid regardless of the size of the individual or the size of the forearm and hand under consideration. However, it has been found that some individuals, perhaps as a result of a prior injury to the wrist, cannot tolerate elevating their hand 70° relative to their forearm. In such case an angle less than optimum, for example 60°, can be used and although optimum visibility is not obtained, this is the best available information, and an experienced physician can obtain acceptable results. It should be noted that if an insert is used at a less than optimum angle that same insert must be used in subsequent X-ray pictures. The prior art includes devices for supporting human body members in a variety of different positions to facilitate X-rays. However, the known devices are adjustable devices that are designed to exert stress on the body parts being examined and lack the means for properly aligning and assuring that the a precise angle for a particular condition will be used at all times. Such devices are shown in the U.S. Pat. Nos. 3,521,976; 4,045,678; 4,320,749 and 4,323,080.

It is therefore a primary objective of the present invention to provide a device that can retain a patients limb in a precise angular relationship to optimize the revelation of the x-ray for a particular condition under consideration.

Another objective of the present invention is to provide a device for posing a patients limb for use when a series of x-rays are required to chart the progress of a condition and it is critical that the limb must be in the identical angular position in all x-rays.

Another objective of the present invention is to provide a device for posing the wrist, of patients suffering from carpal tunnel syndrome, for x-rays that will optimize the revelation of the x-ray in treating the patients carpal tunnel syndrome.

Still another objective of the present invention is to provide a device for posing the joints of patients suffering from joint disorders, that can accept replaceable inserts that have been designed to support the joint at a precise predetermined angle.

SUMMARY OF THE INVENTION

Briefly, a preferred embodiment of the present invention includes a carriage to which a patients forearm and hand can be secured by restraining mechanism such as straps at a prescribed angle that will enable the physician to evaluate the patients condition such as carpal tunnel syndrome.

An important advantage of the present invention is that the physician's knowledge of the patients condition is maximized with minimum exposure to x-rays. It is another advantage of the present invention that the progress of the condition being treated can be charted by comparing a series of x-rays all of which were taken at the identical angle.

Another advantage of this invention is that a series of X-rays of a body joint taken at a precise predetermined angle, that has been found to display the patients bony structure at an optimum posture, are obtained which are essential to record progress that has been made in the treatment and to prescribe future treatment.

These and other objects and advantages of the present invention will no doubt become apparent to those skilled in the art after having read the following detailed description of the preferred embodiment which are contained in and illustrated by the various drawing figures.

DETAILED DESCRIPTION OF THE PREFERRED EMBODIMENT

Figure 1:
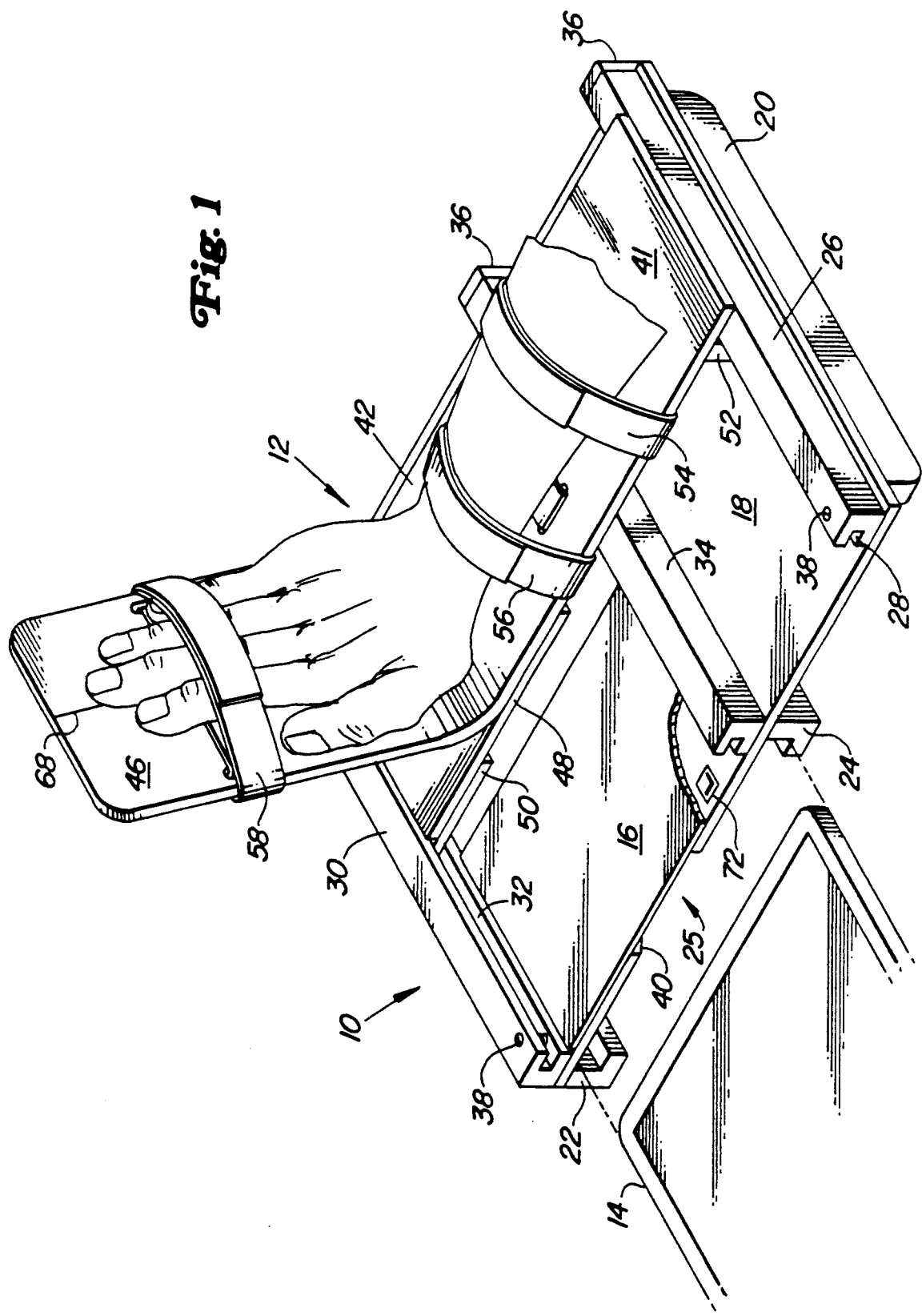
FIG. 1 is a perspective view of the poser with the X-ray plate and the lead shield projected out of their normal location.

FIG. 1 is a perspective view of the X-ray poser showing a patients hand and arm held by straps on a carriage that is contoured to cause the hand to be bent at a precise angle to the forearm.

Figure 3:
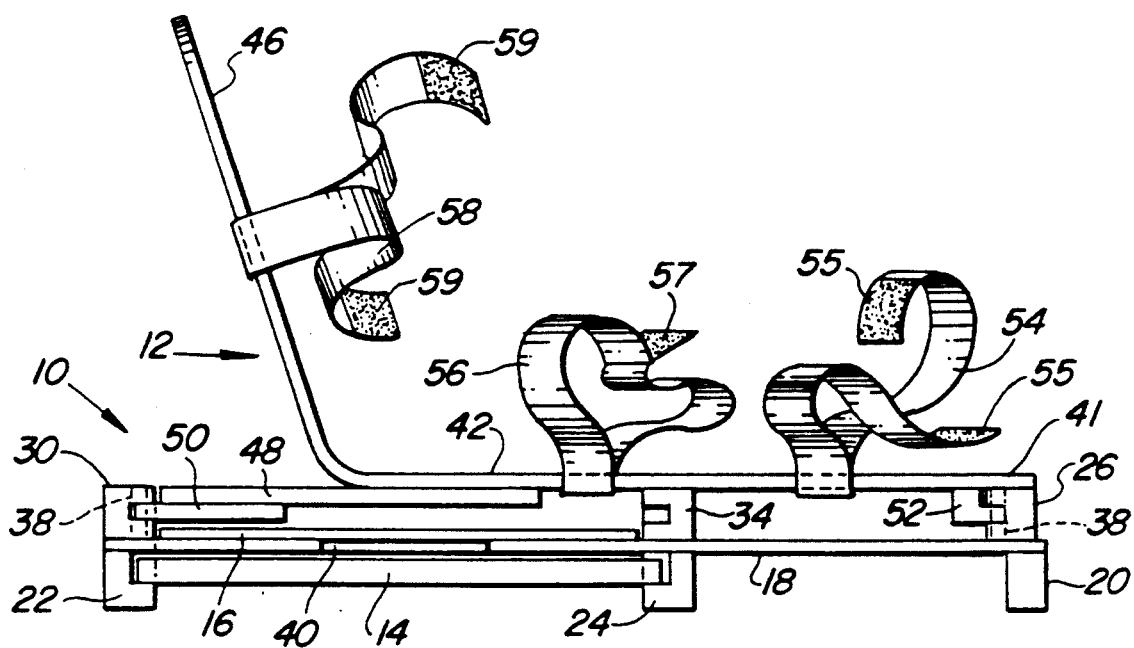
FIG. 3 is a side view of the X-ray poser without a patients arm and hand secured thereto.

The support plate 42 is made of a single piece of material and includes a horizontal section 41 and an inclined section 46. The support plate 42 is made for example of plexiglass and is bent at an angle of 70° between the horizontal section 41 and the inclined section 46. A bottom plate 48 is secured as by adhesive to the bottom surface of the support plate 42 such that it extends under the inclined section 46. As best seen in FIG. 3, a slide rail 50 is secured as by adhesive to the bottom surface of the bottom plate 48 such that it extends beyond the free end of bottom plate 48 and its free edge is aligned with groove 32 formed in slide bar 30. An L-shaped slide rail 52 is secured as by adhesive to the bottom surface of the support plate 42 adjacent the edge opposite the slide rail 50. A first strap 54 including a velcro connector 55 is connected to the support plate 42 in the horizontal section 44 and extends around the patients forearm. A second strap 56 including a velcro connector 57 is connected to the horizontal section 41 of the support plate 42 and connected around the patients wrist. A third strap 58 including a velcro connector 59 is secured to the inclined section 46 of the 42 and extends around the patients fingers. The patients forearm and hand are secured to the carriage 12 with the hand bent at precisely 70° to the forearm. This is the optimum angle for an X-ray to be helpful in the diagnostics and treatment of carpal tunnel syndrome. As treatment progresses the patients forearm and hand will be again connected to the carriage 12 and X-rayed. The previous and current X-ray results can then be compared and the physician is confident that the arm and hand were at the same angle in both X-rays. To assemble the carriage 12 on the stationary platform 10 the stop 38 must be removed. The free edge of the slide rail 50 is aligned with the grove 32 of the slide bar 30 and the L-shaped slide rail 52 is aligned with the groove 28 of the first slide bar 26. The carriage 12 is then slid to the right as seen in FIG. 1. As the carriage 12 reaches the position on the stationary platform 10 as illustrated in FIG. 1 the lower surface of the support plate 42 is in sliding contact with the upper flat surfaces of the first slide bar 26 and mid location slide bar 34 and slide rail 50 is engaged in grove 32. Provided the X-ray poser is being assembled the stop 38 would now be secured in place to prevent the inadvertent separation of the carriage 12 from the platform 10. The stops 38 can be easily removed and replaced with a simple tool such as a screw driver. It has been found that there are occasions when it is desirable to remove the carriages and replace it with an inserts carriage that has a different design than the original carriage. The portion of such an insert carriage that interacts with the platform 10 is of course identical to the corresponding portion of the original carriage 12 however, for example, the inclined portion of the support plate may be at a different angle. Also inserts have been developed for posing the wrist, hand, elbow, foot, ankle and knee at optimum positions. Such additional inserts can be quickly and easily installed in the platform. Each insert has a permanently affixed radiopaque marker that will be visible in the processed X-ray so that the physician has a permanent record of the insert that was used for that particular X-ray. This feature is of particular value when a series of X-rays are required over a time span. In this situation such markers show at a glance that all X-rays in the series were taken on the same insert.

It should be noted that the carriage 12 can be slid to the right as seen in FIG. 1 for a purpose to be discussed later. The first and second L-shaped base members 22 and 24, respectively, are located relative to each other such that they define a film receiving compartment 25 for the reception of a standard size X-ray plate 14 or cassette, for example a ten inch by 12 inch plate. A third base member 20 supports the other end of base plate 18. Base members 20, 22 and 24 all have non-glide surfaces on their lower surfaces to prevent the X-ray poser from sliding on the surface that is supporting it. The bottom surface of the base plate 18 and the shelf like surfaces of the first L-shaped base member 22 and second L-shaped base member 24 define the film receiving compartment 25. The X-ray plate 14 is slid in the film receiving compartment 25 until it is completely within the film receiving compartment 25. In this position the edge of the film receiving compartment 25 can be grasp as a result of the notch 40. When the film receiving compartment 25 is fully inserted into the film receiving compartment 25 it extends across the entire width of the base plate 18. Since the patients limb requires only portion of the X-ray plate 14 it is possible to use a single X-ray plate 14 for two X-rays of a patients wrist. This process will be discussed in greater detail later in the specification. When the X-ray plate 14 has been fully exposed the physician grasps the edge that is exposed by the 40 and processes the X-ray plate 14. The lead plate 16 is dimensioned to cover approximately half of the surface area of the base plate 18 between the second slide bar 30 and mid location slide bar 34. As indicated in FIG. 1 when carriage 12 is located as shown in this figure the lead plate 16 can be placed to its right and when so placed will shield the portion of the X-ray plate 14 below it from exposure while the other half of the X-ray plate 14 is used to X-ray the patients wrist. After the left half of the X-ray plate 14 has been exposed the carriage 12 can be slid to the right, the lead plate 16 moved from the right to the left and a second exposure made on the X-ray plate 14. The lead plate 16 rest on the upper surface of base plate 18 and thus can be slid from one side of the platform 10 to the other.

The X-ray poser is constructed such that it is convenient and comfortable for the patient if his right wrist is X-rayed when the carriage 12 is slid to its right hand position and his left wrist is X-rayed when the carriage 12 is slid to its left hand position. The platform 10 has a left 72 (see FIG. 1) and a right radiopaque marker affixed to the base 18 that will be seen in the processed X-ray to identify the extremity that was X-rays after the film is processed. This was accomplished in the past by the X-ray technician manually taping a Left or Right radiopaque marker to the carriage. That method was not only time consuming but had the potential for error.

FIG. 1 provided a complete understanding of how the various components of the X-ray poser functions and how two exposures can be obtained on a single X-ray plate 14.

Figure 2:
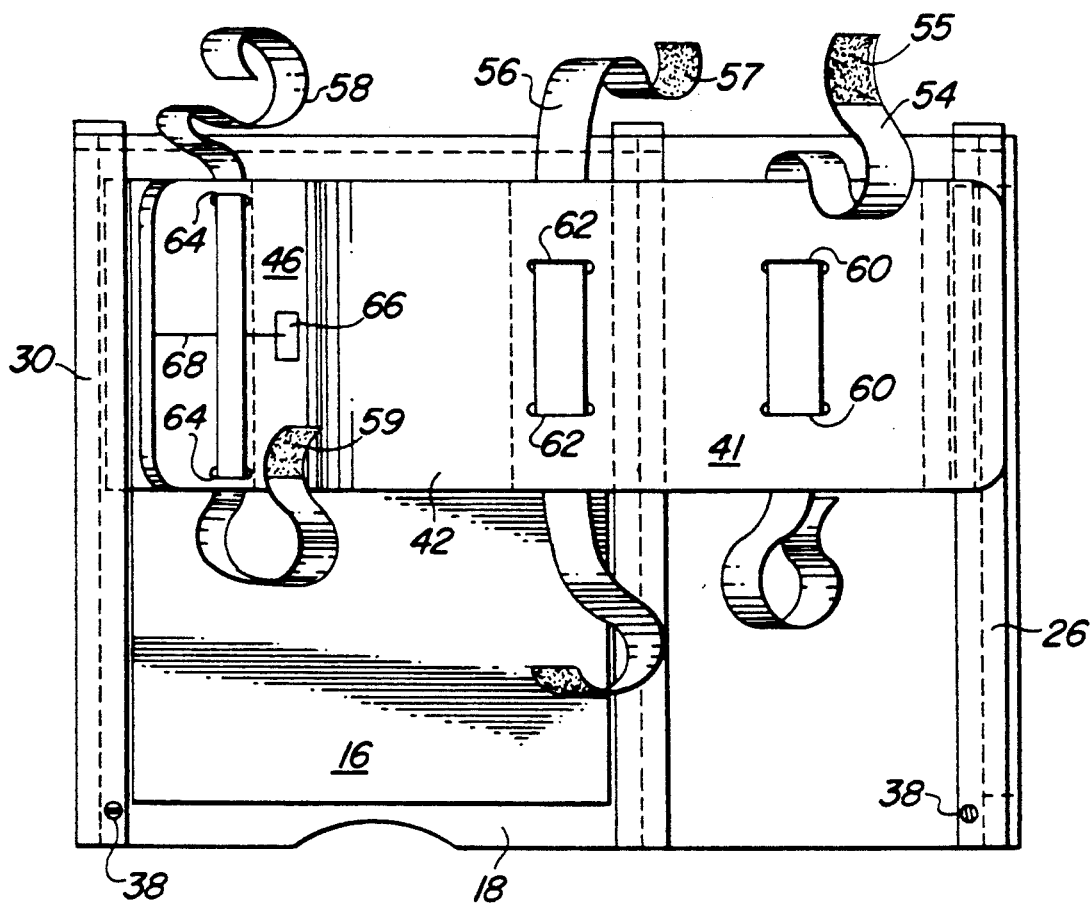
FIG. 2 is a plan view of the X ray poser showing the carriage in the opposite position from that shown in FIG. 1 and without a patients arm and hand secured thereto.

FIG. 2 is a plan view of the X-ray poser before the patients arm and hand have been strapped into place on the carriage 12. In this view the aligning indicia for properly locating the patients wrist on the carriage is visible. Also in this figure the slots for restraining the straps on the support plate 42 as well as the velcro connectors 55, 57 and 59 on the straps are illustrated.

The base plate 18 is slidable in the grove 32 and groove 28 of the platform 10 from the position shown in FIG. 1 to the position shown in FIG. 2. After the carriage 12 has been displaced from its FIG. 1 position to its FIG. 2 position the lead plate 16 would be slid from its FIG. 1 position, to the right of the 12 to its FIG. 2 position. The lead plate 16 rest on the upper surface base plate 18 and there is sufficient clearance between base plate 18 and the undersurface of carriage 12 to permit the lead plate 16 to be slid beneath the carriage 12. The wrist target area 66 and index finger line 68 are etched into the plexiglass of the inclined section 46 of the support plate 42 to assist the physician as well as the patient in properly aligning the patients arm and hand on the carriage 12. When the physician is satisfied that the patients arm and hand are properly aligned he grasp the opposite ends of each strap, pulls them taut across the upper surface of the patients arm and had and connects them together with the velcro fasteners. It should be noted that the first strap 54 is connected to the support plate 42 by passing each free end of first strap 54 downwardly through the first set of slots 60 formed in the horizontal section 44 of the support plate 42, across the bottom surface of the horizontal section 44 and then up where the ends can wrap around the patients fore arm to secure it is place on the horizontal section 44. There is a second set of slots 62 formed in the horizontal section 44 for reception of the second strap 56 and a third set of slots 64 for reception of the third strap 58.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A device for positioning and holding a patient's joint for radiographic comprising:
    a stationary platform including a generally horizontal base plate having an upper and a lower surface,
    a pair of slide bars extending upwardly from the upper surface of said base plate,
    said slide bars being parallel to each other and each having a horizontal groove formed therein,
    said horizontal grooves opening toward each other;
    a carriage including a pair of slide rails received in and slidable along said horizontal grooves to slidably mount said carriage on said stationary platform,
    said carriage having a longitudinal axis and being elongated in its longitudinal direction, said slide bars being mounted on said base plate such that they extend perpendicular to the longitudinal axis of said carriage such that the carriage slides normal to its longitudinal axis,
    said carriage including a horizontal section that includes restraining mechanism adapted to restrain a portion of a patient's extremity adjacent a joint, and
    an inclined section, formed integral and rigid with said horizontal section, including restraining mechanism adapted to restrain another portion of a patient's extremity on the other side of said joint such that said portions of the patient's extremity are restrained at a selected fixed angle.

2. The invention as set forth in claim 1, wherein said inclined section of said support plate is inclined to said horizontal section at an angle that will pose the joint at an optimum angle to analyze a particular condition.

3. The invention as set forth in claim 2, in which said optimum angle is 70°.

4. The invention as set forth in claim 1, wherein said stationary platform includes a film receiving compartment located below the lower surface of said generally horizontal base plate, and
    said film receiving compartment being of a size and shape such that it can receive a standard X-ray sheet.

5. The invention as set forth in claim 4, in which the portion of said carriage that overlies said film receiving compartment is of a size and shape that when slid from one location to the other it will overlie separate and distinct potions of said film receiving compartment.

6. The invention as set forth in claim 1, wherein said carriage includes aligning indicia permanently affixed thereto for properly aligning the patients extremity thereon.

7. The invention as set forth in claim 1, wherein said stationary platform includes a plurality of radiopaque markers fixed to said base plate that will be visible in the processed X-ray and will indicate where relative to the base plate the X-ray was taken.

8. The invention as set forth in claim 1, wherein said restraining mechanisms are in the form of straps having mating velcro fasteners on their opposite ends to facilitate the restraining and release of the patients extremities.

9. The invention as set forth in claim 8, wherein there are two such restraining means on the horizontal section of said carriage.

10. The invention as set forth in claim 1, wherein a lead sheet rests on said upper surface of the base plate and is slidable thereon,
    said lead sheet being of a shape and size that it can be slid across the surface of the base plate from a first location to a second location so that when said lead sheet is in the first location a portion of an X-ray film corresponding to the shape and size of the lead sheet will be shielded, and when it is in the second location another portion of the X-ray film, corresponding to the size and shape of the lead sheet will be shielded.

11. The invention as set forth in claim 1, wherein stops are provided in said grooves to prevent the unintentional release of said carriage from confinement in the grooves of said stationary platform.

12. The invention as set forth in claim 11, wherein at least one of said stops are easily removable and replaceable to permit replacement of the existing carriage with a different insert carriage.

13. A device for restricting the portions of a patient's extremity on both sides of a joint to a preselected position and attitude for radiographic purposes comprising:

a stationary platform including a generally horizontal base plate having an upper and a lower surface, a pair of slide bars extending upwardly from the upper surface of said base plate, said slide bars being parallel to each other, a carriage including a pair of slide rails, said slide bars and slide rails each including cooperating slide mechanism that function to slidably mount said carriage on said stationary platform, said carriage including a horizontal section that includes restraining mechanism adapted to restrict a portion of a patient's extremity adjacent a joint at a preselected position and attitude on said horizontal section such that in subsequent uses of said device the patient's extremity will be restricted to the same preselected position and attitude, an inclined section, formed integral and rigid with said horizontal section, including restricting mechanism adapted to restrict another portion of a patients extremity on the other side of said joint to a preselected position and attitude, and said stationary platform including a film receiving compartment located below the lower surface of said generally horizontal base plate.

* * * * *